US005980449A

United States Patent [19]

Benson et al.

[11] Patent Number: 5,980,449

[45] Date of Patent: Nov. 9, 1999

[54] INFANT WARMER

[75] Inventors: Mark Gregory Benson; Andrew Paul Maxwell Salmon; Christopher Peter Hutchinson; David Valletort Haysom; Richard Barry Doig; Paul Joseph Moody, all of Auckland, New Zealand

[73] Assignee: Fisher & Paykel Limited, Auckland, New Zealand

[21] Appl. No.: 08/870,223

[22] Filed: Jun. 6, 1997

[30] Foreign Application Priority Data

Jun. 7, 1996 [NZ] New Zealand .......................... 286762

[51] Int. Cl.[6] .......................... A61F 7/00

[52] U.S. Cl. .......................... 600/22

[58] Field of Search .................. 600/21, 22; 5/600–620; 108/1, 5–10

[56] References Cited

U.S. PATENT DOCUMENTS

| | | | |
|---|---|---|---|
| 4,312,331 | 1/1982 | Hahmann | 600/22 |
| 4,750,474 | 6/1988 | Dukhan et al. | 600/22 |
| 4,809,677 | 3/1989 | Mackin et al. . | |
| 5,162,038 | 11/1992 | Wilker . | |
| 5,376,761 | 12/1994 | Koch et al. . | |
| 5,498,229 | 3/1996 | Barsky et al. | 600/22 |
| 5,817,002 | 10/1998 | Donnelly et al. | 600/22 |

*Primary Examiner*—Samuel Gilbert
*Attorney, Agent, or Firm*—Trexler, Bushnell, Giangiorgi & Blackstone, Ltd.

[57] ABSTRACT

An open care bed or infant warmer having a mattress supported on a mattress base cantilevered from a columnar or vertically disposed "back bone". The column carries an infrared radiant heater head at its upper end which directs heat down towards the mattress. The lower end of the column sits on a base of the infant warmer which is provided with castors for transporting the warmer. The mattress base comprises a box like frame over which a sheet is stretched to provide tensioned support for a mattress. The sides of the mattress base are provided with fold down side walls which are normally retained in a vertical position but are lowerable to a horizontal position, by free falling under the control of a friction controlled damping axle configuration. Adjustment of the angle of inclination of the mattress base is made possible by the use of a non-parallel arm type system providing a virtual pivot point for the mattress base which may be positioned near the center of the mattress.

9 Claims, 8 Drawing Sheets

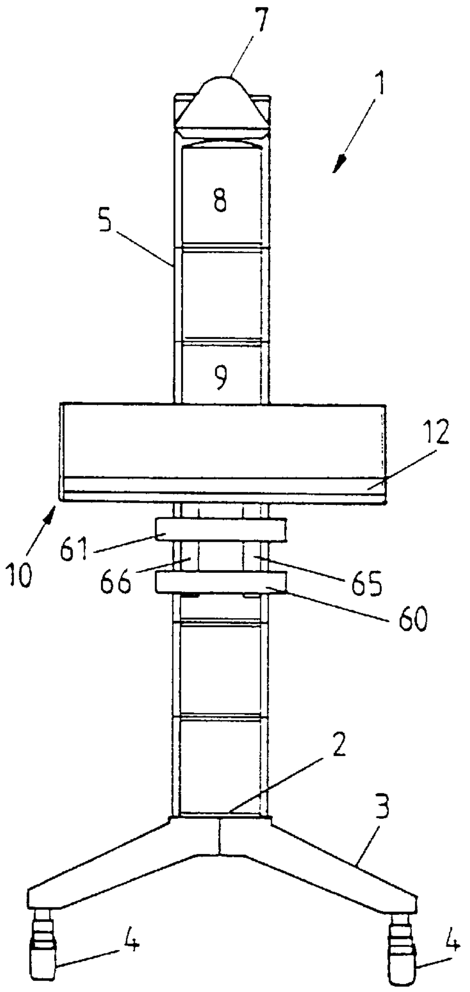
FIG 1
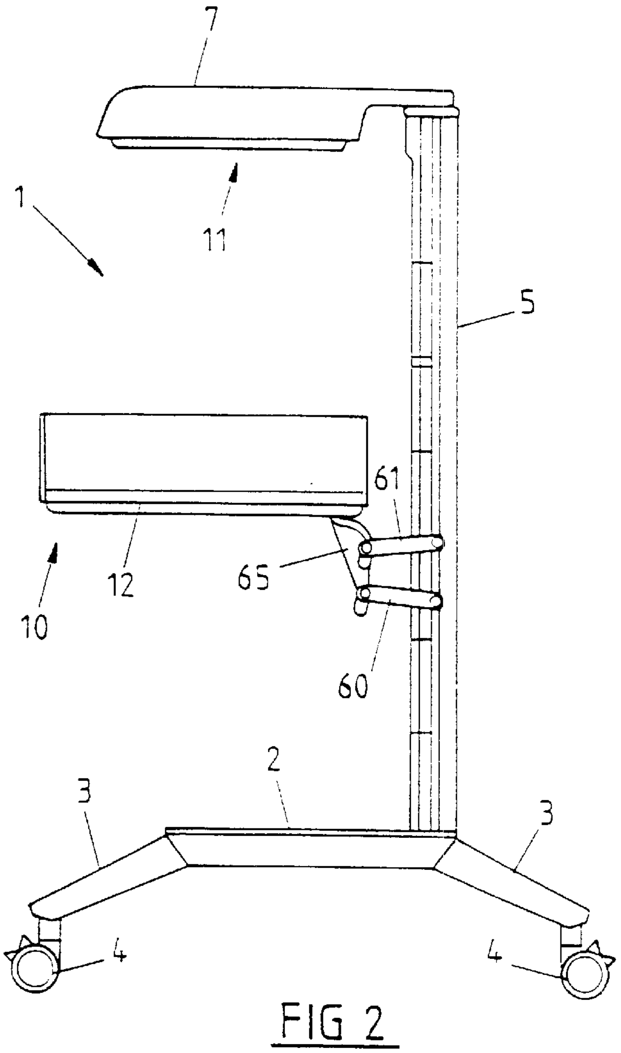
FIG 2
FIG 3
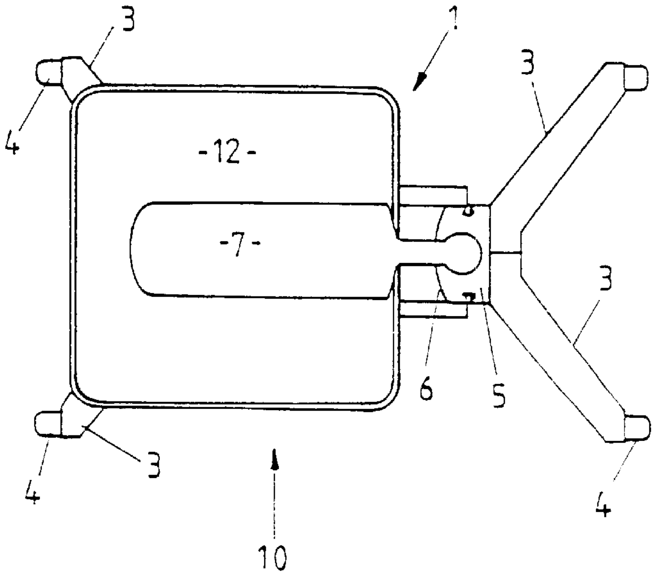

INFANT WARMER

FIELD OF THE INVENTION

This invention relates to infant care centres and in particular though not solely to infant warmer open care beds for providing an easily accessible open care environment to infants in maternity and new born care facilities and the like.

DESCRIPTION OF THE PRIOR ART

A new born infant requiring medical attention may be placed in either a closed care bed such as an incubator or an open care bed such as an infant warmer. In general an infant wanner has the advantage that a medical care giver has immediate, unlimited and unhindered access to the infant while temperature regulation of the infant is more difficult as the infant is exposed to ambient temperature and air flows.

In most existing infant warmers (warmers) the infant is placed upon a padded or pliable mattress on a support surface beneath a radiant heat source. The infant is partially shielded from draughts by low walls which also serve to restrain the infant from falling from the warmer. Examples of this type of support surface are disclosed in U.S. Pat. No. 4,809,677 issued to the BOC Group, U.S. Pat. No. 5,162,038 issued to Hill-Rom Company and U.S. Pat. No. 5,376,761 issued to Ohmeda Inc.

In each of these prior infant warmers the walls of the mattress support surface are removable although removing the walls entails physically pulling the wall from the support structure and then finding a place to store the removed wall. This procedure can often slow down a care giver and/or aggravate an infant or baby. In addition, the matress support is bulky and not collapsible so that assembling/disassembling is often not possible or practical for medical personnel and the removal and relocation of the warmer between two locations accordingly involves large, difficult to handle components.

Another drawback due to the solid construction of these prior warmers is that the mattress support surface is itself usually supported by a solid column such that there is no room beneath the mattress support to position medical equipment such as mod portable x-ray machinery. Furthermore, it is often desirable to tilt the mattress forward or backward of horizontal. In prior warmers, this has been accomplished by placing the mattress support surface on a fulcrum or pivot point, The fulcrum or pivot point has necessarily been mounted on a supporting base further reducing the useable area beneath the mattress support.

BRIEF SUMMARY OF THE INVENTION

It is, therefore, an object of the present invention to provide an infant warmer which goes at least some way towards overcoming the above disadvantages or which will at least provide the industry with a useful choice.

For the purposes of clarity, the main statements of invention will be designated A, B, C and D respectively.

A. Accordingly, in a first aspect, the invention consists in a partially enclosed article support structure comprising:

- a support surface adapted to receive an article,
- at least one article retaining wall means,
- axle means provided on said at least one article retaining wall means,
- axle receiving means provided on said support structure, wherein said at least one article retaining wall means is rotatably attached to said support surface by the mounting of said axle means within said axle receiving means thereby allowing said at least one article retaining means to be rotated from a raised retaining position to a lowered article access position.

B. In a second aspect, the invention consists in a tensioned article support structure comprising:

- rigid frame means having an outer perimeter surrounding an open central portion,
- flexible article support surface means having a continuous edge,
- beading means attached to said flexible article support surface means around a substantial part of said continuous edge, and wherein said flexible article support surface means is adapted to directly support an article which is supported indirectly by said rigid frame means.

C. In a third aspect the invention consists in an inclination adjusting linkage arrangement for a supporting surface to connect said support surface to a fixed structure means, said linkage arrangement comprising:

- first linkage member means having proximal and distal ends, pivotally connected to said fixed structure means at said proximal end at a first position on said fixed structure means,
- second linkage member means having proximal and distal ends, pivotally connected to said fixed structure means at said proximal end at a second position on said fixed structure means, there being a first predetermined distance between said first and second positions,
- wherein the distal ends of said first and said second linkage members arc each pivotally connected to said supporting surface at third and fourth positions respectively, there being a second predetermined distance between said third and fourth positions which is not equal to said first predetermined distance,
- the inclination of said supporting surface relative to the fixed structure thereby being selectable by pivotal movement of said first and second linkage member means about said first, second, third and fourth position.

D. In a fourth aspect the invention consists in an infant warmer comprising;

- base means,
- support column means having a lower end mounted on said base means,
- a partially enclosed article support structure as set out in paragraph A connected to said support column at a predetermined distance from said lower end, and
- radiant heater means connected to said support column means, at a distance from said lower end greater than said predetermined distance, directed towards said partially enclosed article support structure.

BRIEF DESCRIPTION OF THE DRAWINGS

One preferred form of the present invention will now be described with reference to the accompanying drawings in which;

FIG. 1 is a front elevation of an infant warmer constructed in accordance with the present invention, FIG. 2 is a side elevation of the infant warmer shown in FIG. 1, FIG. 3 is a plan elevation of the infant warmer shown in FIG. 1.

DETAILED DESCRIPTION OF THE PREFERRED EMBODIMENT

Infant Warmer Construction

Figure 4:
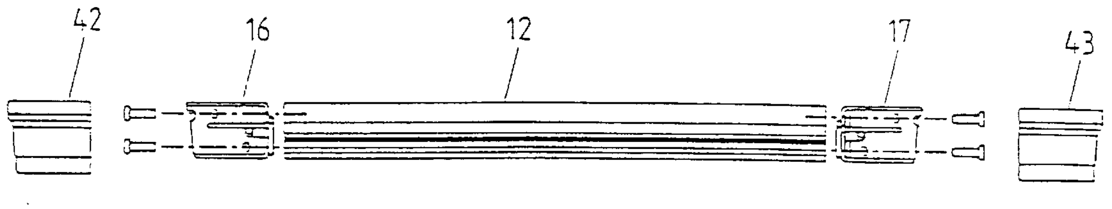
FIG. 4 is an exploded up-side-down side elevation of one frame member from the mattress support structure of the infant warmer shown in FIG. 1.

With reference to the accompanying drawings and in particular FIGS. 1, 2 and 3, one preferred embodiment of an infant warmer open care bed 1 (referred to as "warmer" hereinafter) constructed in accordance with the present invention is shown. The infant warmer has a base portion 2 to which legs 3 are attached. Castors 4 are provided at the ends of the legs 3 to allow the warmer to be easily moved. A support column means, for example column 5 is mounted on base 2. In the preferred form, the column 5 comprises a "U" or "C" shaped aluminium extrusion with an open side 6.

The column 5 acts as a "back bone" to the wanner and serves two main functions, firstly to support a radiant heater head unit 7 at or near the upper end of the column and a partially enclosed article support structure or basinet 10 cantilevered near the centre of the column, and secondly, for mounting a number of modular specific healthcare units, for example temperature control unit module 8 and resuscitation module 9 which are easily slotted into the open side 6 of the column extrusion and supplied with the necessary voltage, gases, etc. The basinet and its connection to column 5 will be further detailed below. The front panel of each module is provided with a cover plate having the required input and/or output sockets for connecting medical equipment such as breathing circuit conduits, and temperature sensors. The spaces in the extrusion which are not being utilised by a module may be covered by a face plate which may easily be removed to allow a further specific module to be retrofitted at a later date.

It can be seen from the drawings that the radiant heater head 7 has an open side 11 through which heat is directed towards a mattress 12 supported on basinet 10. In use, an infant is positioned on mattress 12 and warmed by the heat produced by the radiant heater head 7. The infant is readily accessible for medical treatment and the infant's temperature may easily be monitored (for example by a temperature sensor applied to the infant's skin) with the monitored temperature being fed back to a controller which may then moderate the power supplied to the heater element within the heater head unit 7. This temperature control system could be incorporated into a software program running on a microprocessor within one of the aforementioned modular units inserted into column 5.

Mattress Support (Basinet) Structure

The construction of basinet 10 will now be described in detail with reference to the drawings, in particular FIGS. 4 to 10.

Figure 5:
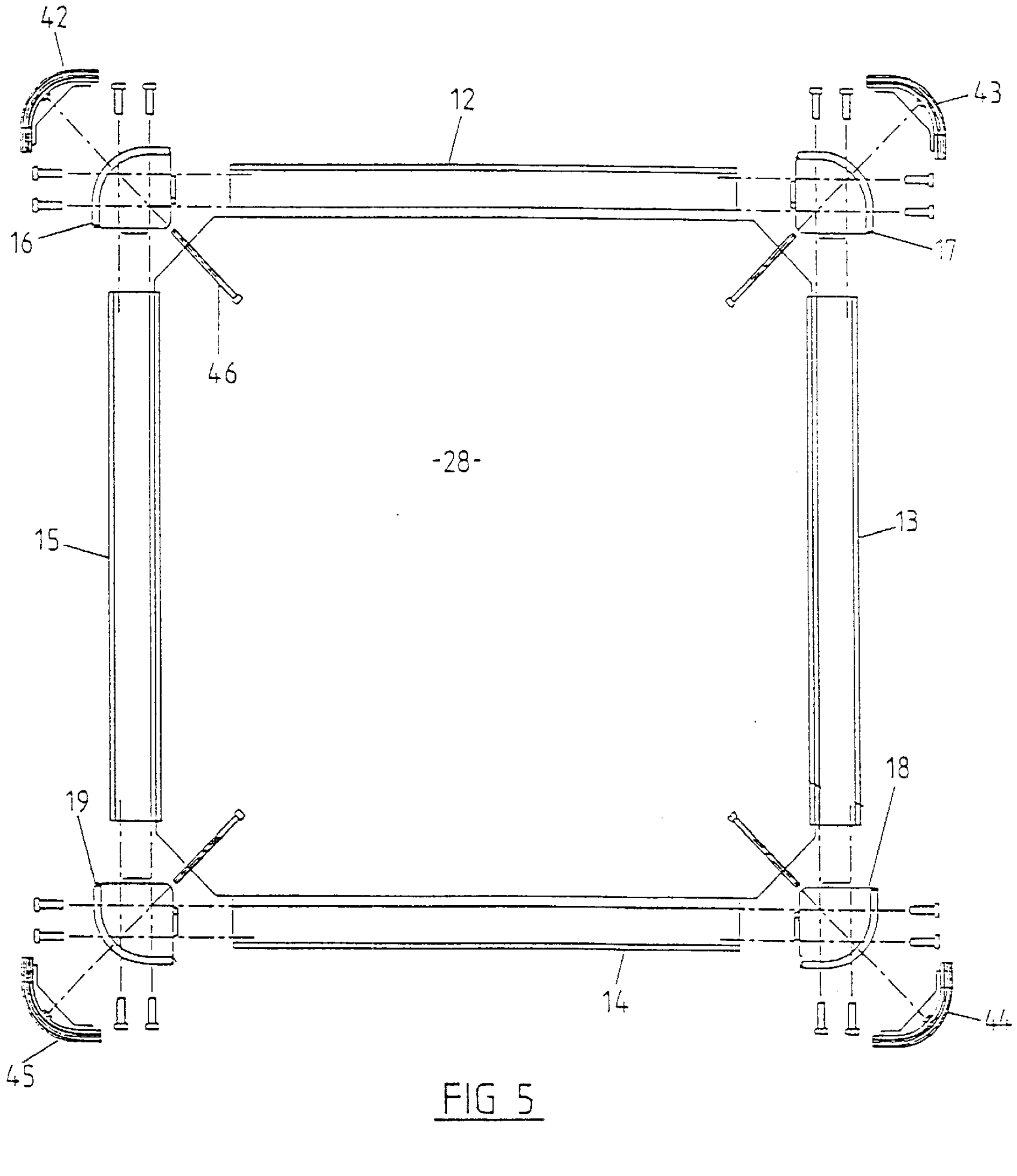
FIG. 5 is an exploded plan view of the mattress support structure of the infant warmer shown in FIG. 1.
Figure 7:
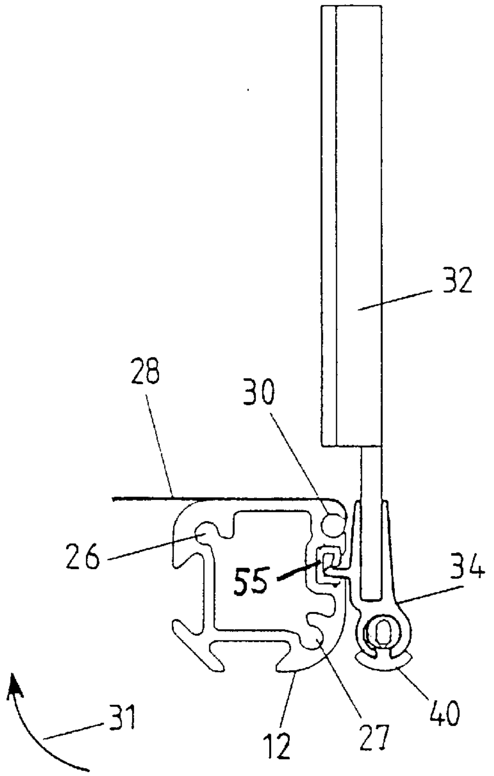
FIG. 7 is a side elevation of a part of the mattress support structure of the infant warmer shown in FIG. 1 with a wall attached.

It can be seen in FIG. 5 that the basinet has a frame preferably comprising our (preferably equal length) rigid frame members, for example basinet extrusions 12, 13, 14 and 15 connected at their ends by corner blocks 16, 17, 18 and 19, supporting a flexible article support surface or mattress base or support 28. Each of the basinet extrusions are preferably light weight aluminium extrusions while the corner blocks are preferably plastic molding or investment cast. The cross-section of each of the basinet extrusions is shown in FIG. 7.

Figure 6:
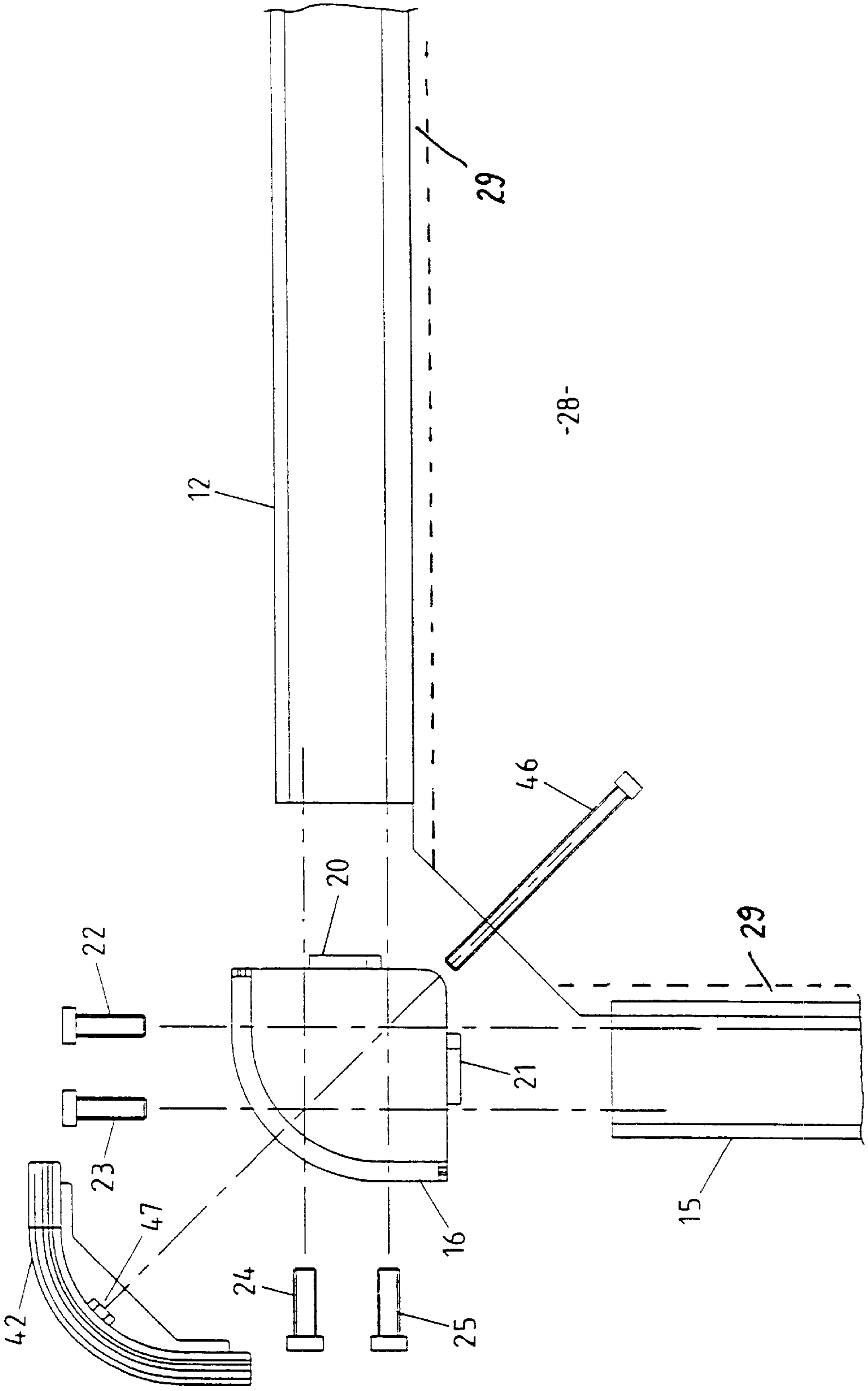
FIG. 6 is an enlarged view of a corner section of the mattress support structure shown in FIG. 5.

FIG. 6 details the connection of two basinet extrusions (12 and 15) with a corner block (16). The corner block has two locating spigots 20 and 21 which fit within the basinet extrusions. In order to hold the corner block to both basinet extrusions, two bolts per extrusion (bolts 22 and 23 for basinet extrusion 15 and bolts 24 and 25 for basinet extrusion 12) are passed through holes in the corner block and into threaded holes, for example holes 26 and 27, within the each extrusion. This is repeated for each comer of the basinet.

A mattress support or base 28 which is preferably a substantially square sheet of material (preferably a light weight polyester with a PVC backing) in use supports a mattress, (preferably a closed cell foam mattress such as polyethylene) adapted to receive an infant. The mattress support material 28 is transparent to x-rays. A bead or piping 29 is formed around the sheet of material by sewing a thin plastics or rubber tube around the perimeter of the material although the corners may be excluded. The bead is inserted longitudinally within an open sided bead receiving slot 30 in the basinet extrusions allowing the mattress support material to be stretched across the frame. Due to the large diameter of the bead compared to the open side of the slot, the beading is not able to be pulled through the open side of the slot. The area of the mattress support material 28 is arranged to be slightly less than the area bordered by the frame to cause the assembled mattress support to be under tension thus providing a flat springy base for a mattress.

In order to assemble the basinet base, the bead around three edges of the mattress support fabric is inserted into the slots in three basinet extrusions which are then bolted together with two corner blocks to form a "U". The beading along the remaining side of material is then fed into the slot in the remaining extrusion and the remaining corner blocks arc then bolted to this last extrusion. At this point, the extrusion which is added last may be rotated about its longitudinal axis in the direction of arrow 31 in FIG. 7 to position the corner blocks to allow the remaining bolts to be inserted. The rotation of the final extrusion tensions the mattress support material to ensure that a firm base is provided on which the mattress may then be positioned.

Mattress Retaining Side Walls

In order to protect an infant from drafts and to stop the infant from falling from the warmer, the basinet is preferably also provided with at least one removable article retaining wall means or side wall 32. In the preferred form four side walls are provided, so that the infant is enclosed on all sides by the warmer except for the side above the infant which is open to the ambient and through which heat is directed from the radiant heater unit 7. Preferably the side walls are manufactured from a tough rigid plastics or acrylic material. Notches, for example notches 37, are provided in the side wall for holding various tubes required for an infant's care.

With reference to FIG. 7, one side wall 32 is shown in its normal raised retaining position, however, the side walls of the basinet according to the preferred form of the present invention are able to fold down to a lowered, article (or infant) access position to allow unobstructed access to the infant. The side wall 32 is taped or crimped within a rectangular channel 33 of a further, preferably aluminium, side extrusion 34. A circular channel 35 is also provided along the length of side extrusion 34 into which a compression spring 36 is inserted. The circular slot may have an open side (as shown) which has a width small enough not to allow the compression spring to escape, alternatively the side wall could be provided with two short slot (one at either end) of, for example, 50 mm in length and two compression springs could be inserted (one in either short slot). The compression spring 36 (or both compression springs) is then compressed by inserting sliding axles 38 and 39 into either end of the circular slot and then the ends of the extrusion are crimped or a split pin or dowel pin is inserted to ensure that the sliding axles are unable to escape from the circular slot. The sliding axles are provided with thumb grips 40 to allow a user to move the sliding axle along the circular slot, facilitating the insertion or removal of the side wall to or from the basinet as will soon be described. The ends of the sliding axle are provided with a profiled stub which is substantially rectangular in cross-section, however the corners are rounded such that the cross-section of profiled stub 41 may be said to substantially form a "race track" shape.

In order to rotatably mount the side walls to the basinet, each of the comer blocks are provided with (preferably plastics) corner block caps 42, 43, 44 and 45 which are positioned over the corner blocks and are bolted to the comer blocks (for example bolt 46 fits into securing threaded hole 47 in comer block cap 42 as shown in FIG. 6).

Figure 9:
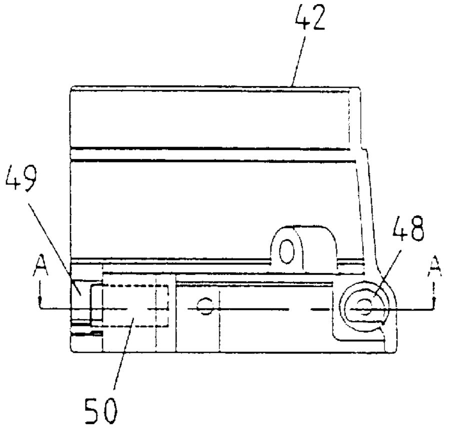
FIG. 9 is a front elevation of a corner block cap assembly shown in FIG. 5.
Figure 10:
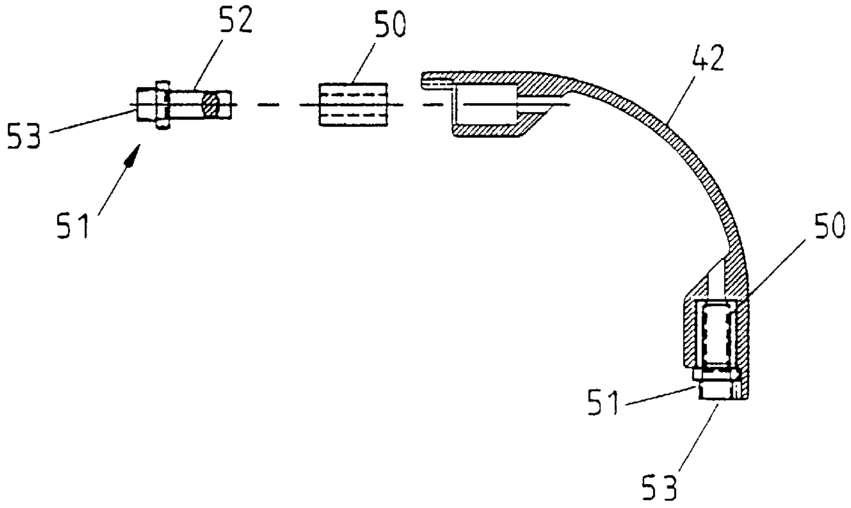
FIG. 10 is a cross-sectional plan elevation through A—A of the corner block cap assembly shown in FIG. 9, FIGS. 11*a*, 11*b*, 11*e*, 11*d*, 11*e* and 11*f* are side elevations of the infant varmer shown in FIG. 1 with the mattress support structure inclined at various different angles
Figures 8A, 8B, 8C:
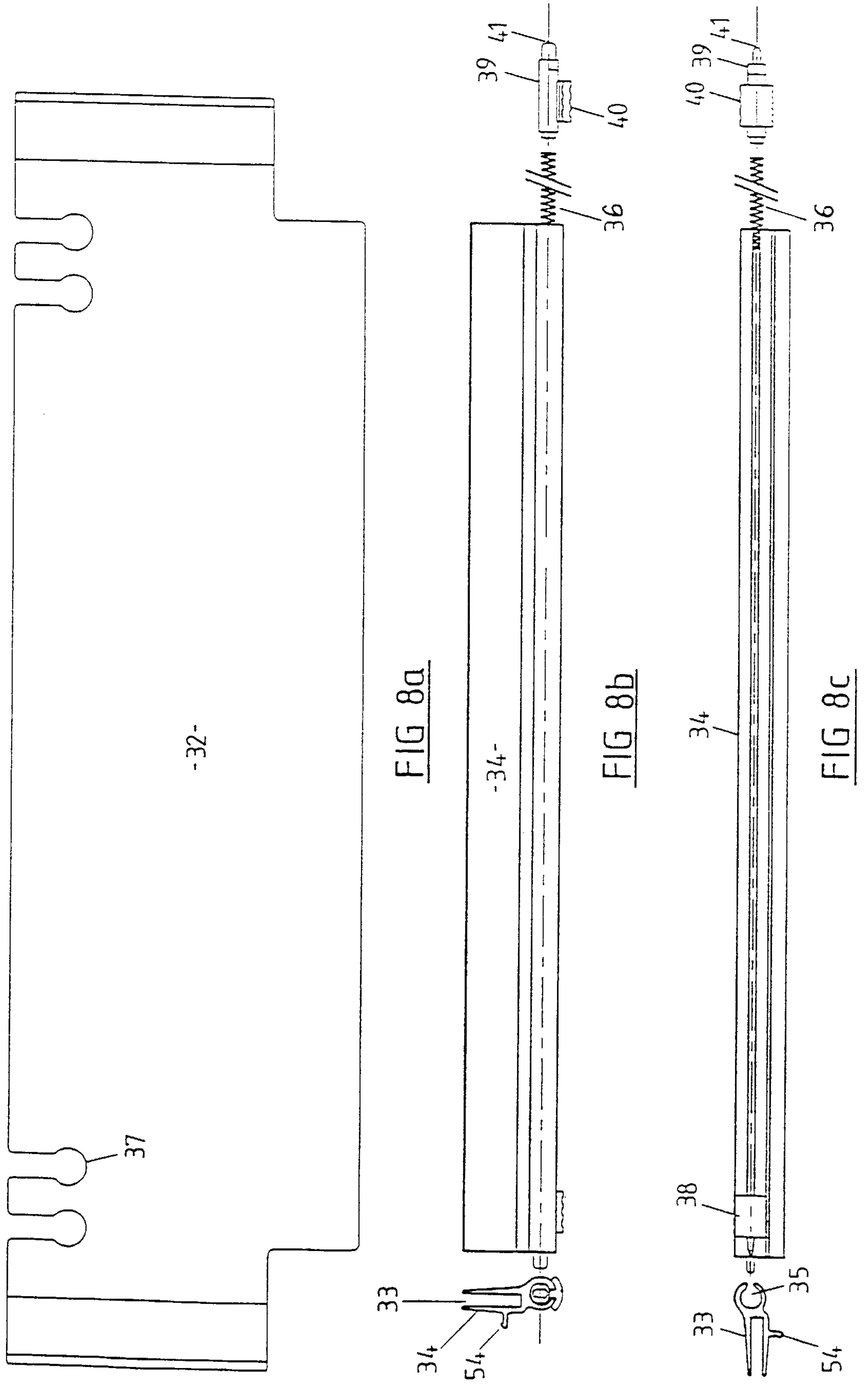
FIG. 8*a* is a front elevation of the infant warmer mattress support structure wall shown in FIG. 7.
FIG. 8*b* is a front elevation of a side extrusion into which the wall of FIG. 8*a* is inserted.
FIG. 8*c* is a plan elevation of the side extrusion shown in FIG. 8*b*.
Figure 11C:
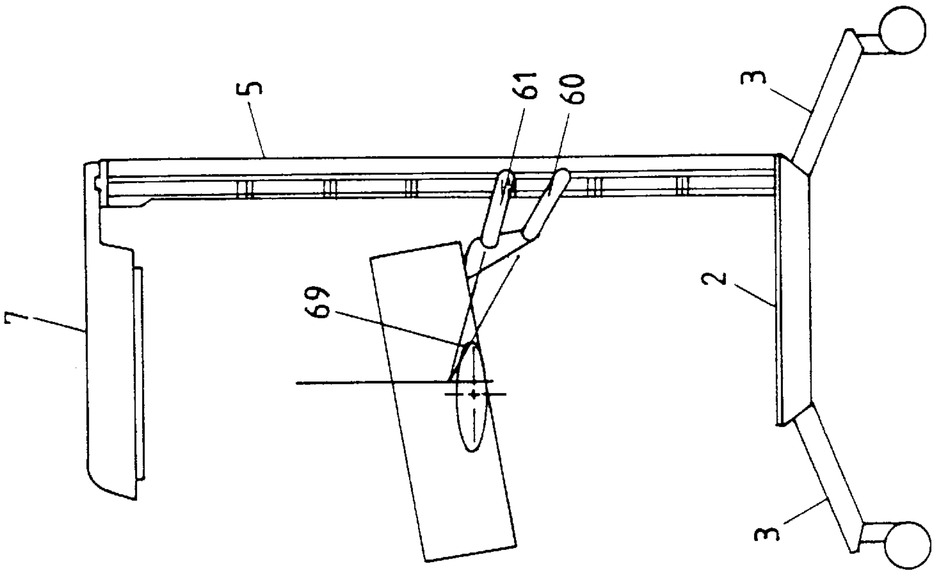
Figure 11B:
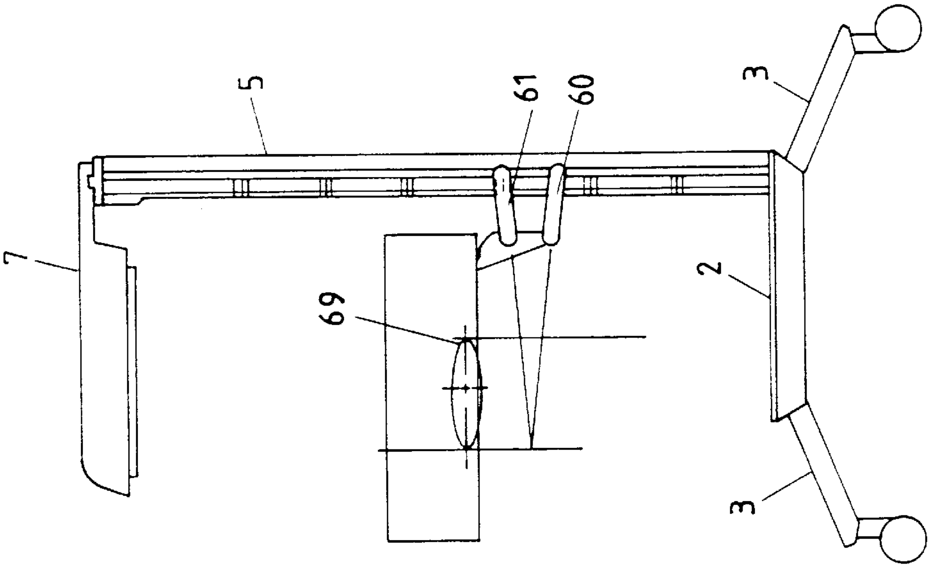
Figure 11A:
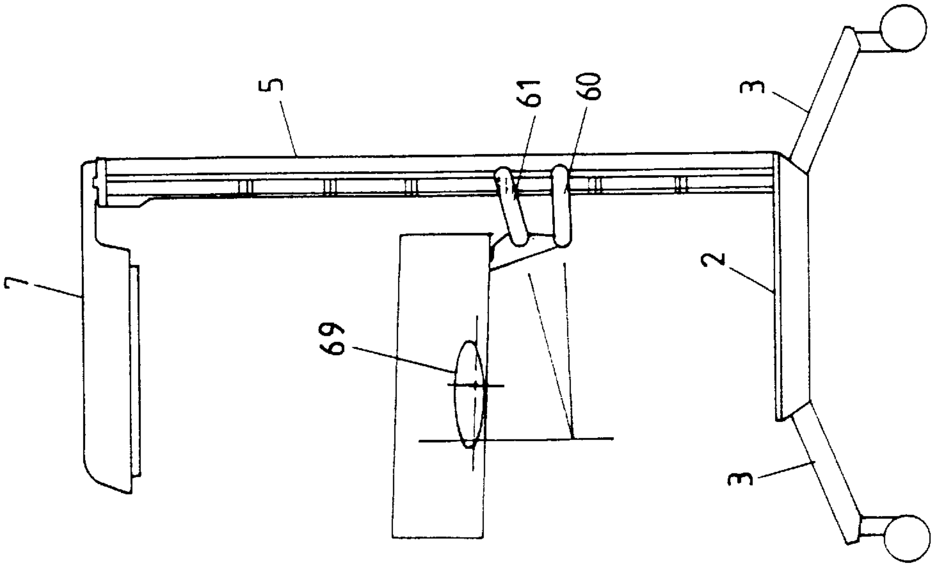
Figure 11F:
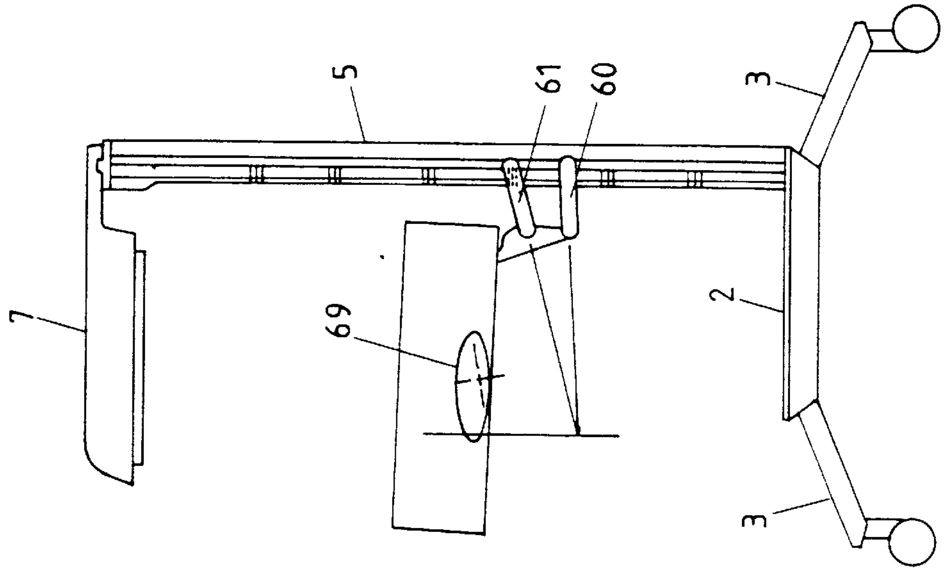
Figure 11E:
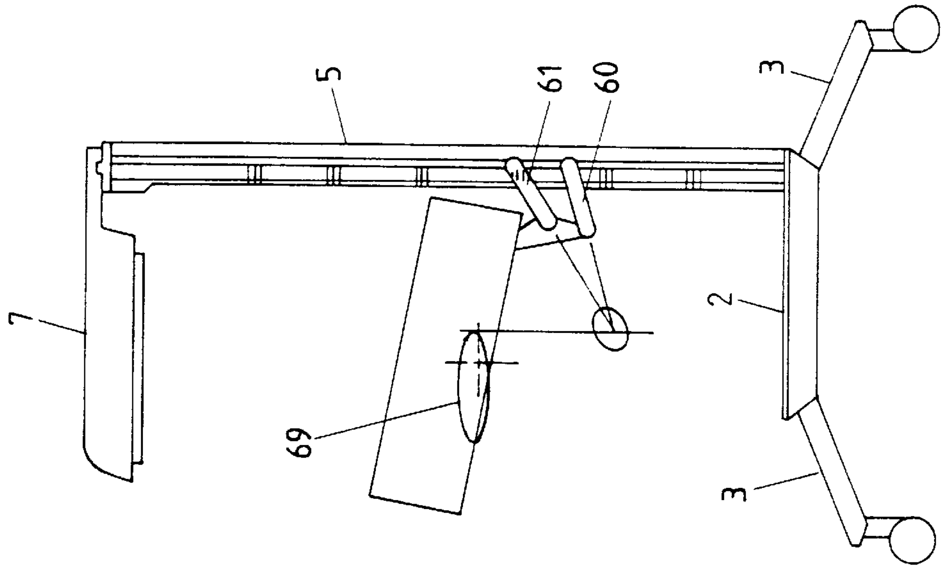
Figure 11D:
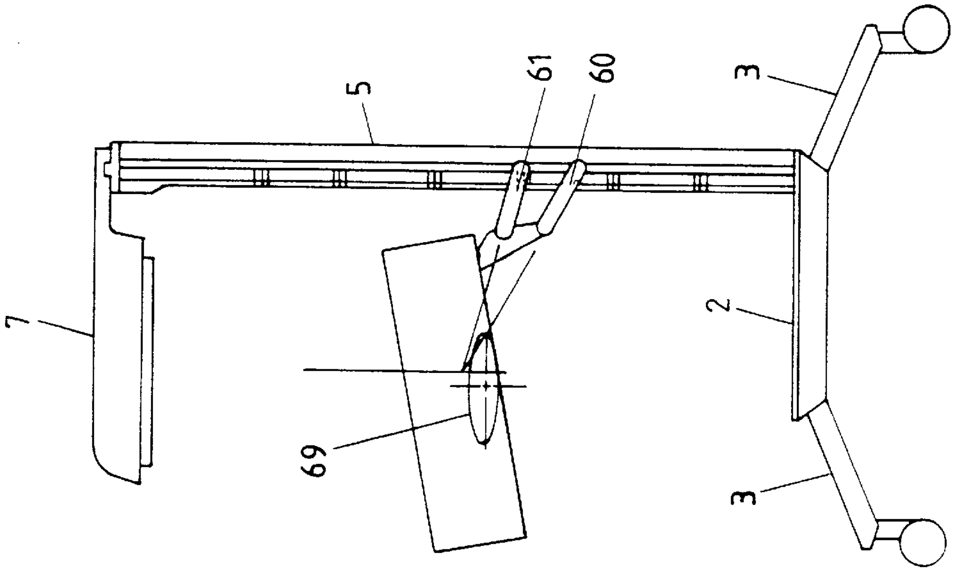

With reference to FIGS. 9 and 10, each corner block cap is provided with two profiled holes 48 and 49 aligned in the same plane as the side and basinet extrusions The profiled holes are substantially circular in cross-section with a segment of the circle removed to leave a substantially "horse shoe" cross-sectionally shaped profiled hole. A compressible cylindrical tube 50 is forced into each profiled hole. The compressible tube may be, for example, manufactured from urethane or any other suitable compressible substance. Upon insertion into the profiled hole the cylindrical tube 50 deforms to the substantially "horse shoe" shape of the hole.

A dummy axle 51, having a tubular portion 52 and a stub axle receiving portion, or profiled locating hole 53, has its tubular portion 52 inserted into the compressed tube 50. The tubular portion has a cross-sectional shape which is substantially elliptical so that the dummy axle will need to be aligned correctly with the profiled hole 53 to allow insertion. Once inserted rotation of the dummy axle will be possible within tube 50 although the ease of rotation will vary depending on the rotational alignment of the tabular portion within the profiled hole. As the widest cross-section of the dummy axle 51 is rotated into alignment with the narrow part of the profiled hole, the friction between the dummy axle 51 and the cylindrical tube 50 will increase. The stub axle receiving portion 53 of dummy axle 51 has an opening which is designed to be a locking fit with the profiled stub of the sliding axles.

Accordingly, in order to assemble the side walls to the basinet, firstly the corner block caps (with their urethane tubes and dummy axles inserted) are bolted to each of the corner blocks. Each of the assembled side walls (with the walls inserted into their extrusions and the axles inserted within their slots) are then in turn positioned adjacent a frame extrusion. The installer must then force the two sliding axles within the side wall extrusion towards the centre of the wall so that the stub axles are withdrawn inside the circular slot. The side wall is then moved into position between two corner block caps with the sliding axles of the wall aligned with the dummy axles of the comer blocks. The installer then allows the sliding axles to spring outwards so that the profiled stubs align with and lock into the profiled openings in the dummy axles. The side wall is then installed. Removal of the side wall is carried out by sliding the sliding axles inwards towards the centre of the side wall and simply removing the wall In order to lock the side wall at its normal operating position, that is its raised position as shown in FIGS. 1, 2 and 7, the wall extrusion is provided with a latching hook 54 which extends out from the side of the extension adjacent the warmer. A plastic clip extrusion 55 (preferably a plastics or rubber extrusion or more preferably a plastic molding) is inserted into a specially designed slot in each basinet extrusion. The plastic clip extrusion 55 allows the latching hook 54 to be inserted with minimal force but requires a larger force to remove the latching hook. Thus the side walls are easily locked into their raised retaining position and will not accidentally be knocked from this position, requiring intentional unclipping by an operator of the warmer. The previously described construction of axle for the side walls allows the sides to be lowered quietly without the user needing to physically guide the walls the entire 180° down. Once unclipped, the user may let go of the side wall and rely on the frictional axle connection to damp the fall of the wall. The wall will eventually reach its lowered access position with no sudden noise or movement which would otherwise startle the infant.

In an alternative preferred embodiment, the interlocking system of the above described dummy axle 51 and sliding axle 38, 39 may be transferred so that the dummy axle 51 is provided with a profiled stub (rather than a profiled hole) and the sliding axles 38, 39 are provided with profiled hoes (rather than profiled stubs)

Basinet Support Mechanism (Non-Parallel Links)

With reference now particularly to FIGS. 1, 2, 11*a* to 11*f* and 12, the above described basinet with removable fold-down sides is attached to the support column 5 by an inclination adjusting linkage arrangement. The linkage arrangement comprises two link members 60 and 61. Preferably each link member is "U" shaped and the two legs of the link member are pivotally attached to either side of the support column 5 at their proximal ends. Preferably, but not necessarily, the link members are the same length. It can be seen in FIG. 12 that link member 61 is connected to the column 5 through pivot point 62 while pivot member 60 is connected to column 5 through pivot point 63.

Preferably a channel 64 is provided in each side of the column and "T" shaped sliding blocks are positioned within the channel so that they may slide up and down the channel but may not be withdrawn therefrom. Preferably the pivot points 62 and 63 are connected into the aforementioned "T" shaped sliding blocks to allow rapid height adjustment of the basinet relative to the support column 5. Upon tightening the screw or bolt connecting the linkage member to its "T" shaped sliding block, the "T" shaped block is firmly frictionally held in position in the channel although still allowing free rotational movement of the linkage members about their connection to the column 5. Upon tightening, it will be observed that a fixed distance (a first predetermined distance) has been set between the two pivot points 62 and 63.

The distal ends of the link members are attached to two mounting brackets 65 and 66 which are connected (preferably screwed) at their upper ends within a specially shaped channel in the basinet extrusion closest to the column 5. The distal ends of the link members 60 and 61 are pivotally connected to the mounting brackets at pivot points 67 and 71 respectively. It can be seen that there is a fixed distance (a second predetermined distance) between pivot points 67 and 71. By ensuring That the first predetermined distance is preferably less than the second predetermined distance, it is possible to adjust the angle of inclination of the basinet with respect to the column 5 to adapt the angle of the infant in relation to medical personnel or medical equipment as the situation dictates (such as to allow surfactant administration to an infant). Thus the juxtaposition of the link members which are constrained to rotate about their proximal pivot points on the column with the added constraint that the distance between their distal ends is fixed, produces a non-parallel linkage arrangement which allows the basinet to be tilted without the need for a large supporting or tilting structure to be positioned directly below the basinet. The area directly below the basinet is thus free to be used for storage or, for example, to allow modem portable x-ray equipment to be positioned directly beneath the infant.

Figure 12:
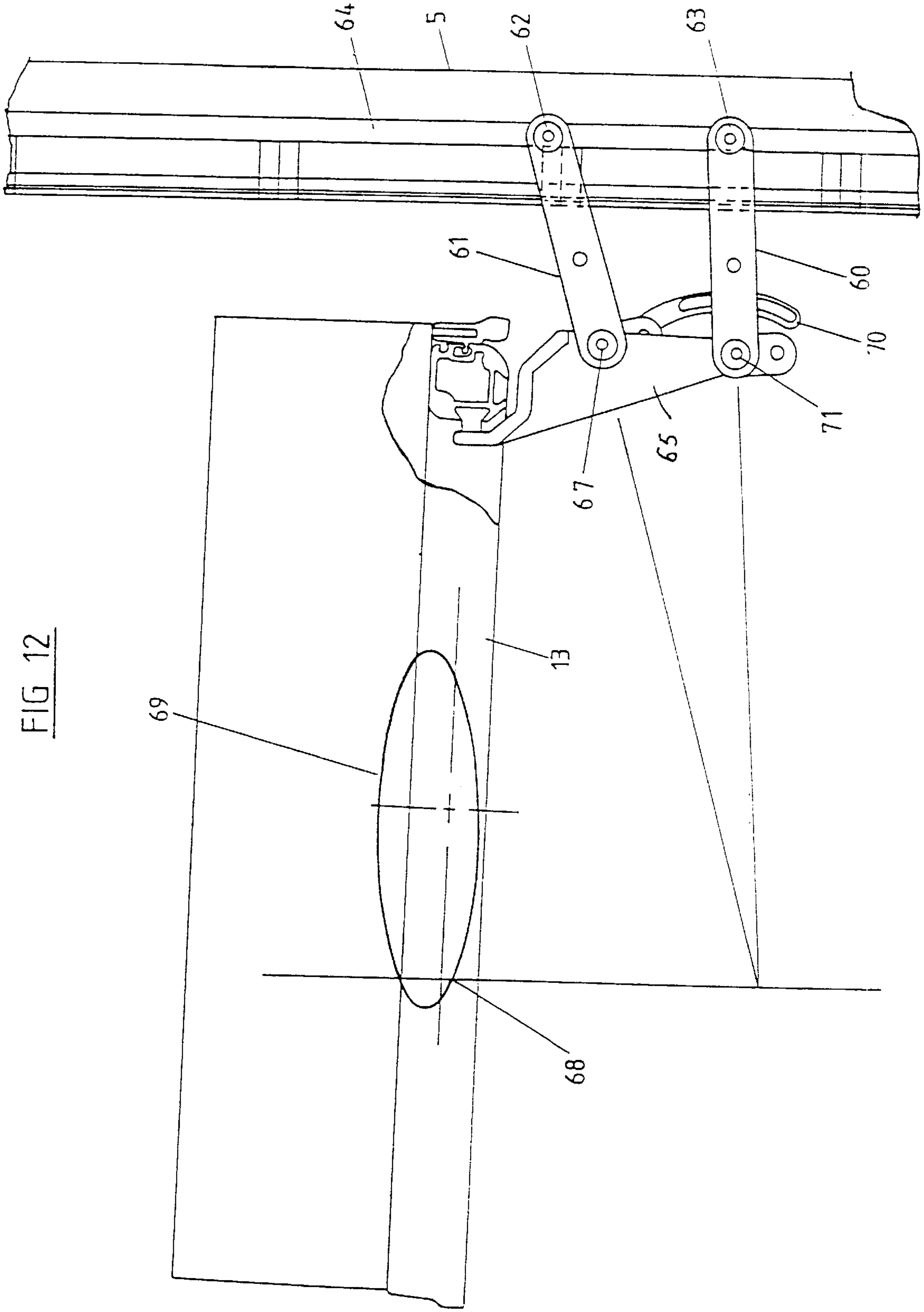
FIG. 12 is an enlarged view of a section of the infant warmer shown in FIG. 11*a* showing the inclination adjustment linkage mechanism.

It has been found that the above described linkage arrangement produces an instantaneous link centre 68 about which the basinet pivots. The instantaneous link centre changes position slightly depending on the basinet angle thus creating a "virtual pivot centre" 69 which comprises the locus of all possible instantaneous link centre positions. It has been found that the virtual pivot centre is substantially elliptical in shape By adjusting the position of the virtual pivot centre (for example by altering the length or positioning of link members 60 and 61), the basinet may be made to pivot about the centre of the mattress (as shown in FIG. 12) which is the optimal position for pivoting an infant supported by the mattress.

A braking mechanism is included in order to lock the basinet into position once a selected angle of inclination has been established. The braking mechanism preferably acts to lock the two link members in position relative to each other. An example of a suitable braking mechanism is a multi-plate brake 70, similar to those utilised in modern office chairs to adjust and lock the seat back angle, basically utilising a friction force to oppose movement. A handle (not shown) may be hidden beneath one of the basinet extrusions with a cable connected to release the multi-plate brake and allow the basinet to be tilted to a new angle at which time the handle may be released and the basinet tilt angle will again be locked. Alternatively a hydraulic piston could be used to provide an opposing force.

Thus, at least in the preferred form, the present invention provides an economical, low cost, low weight and easily assembled infant warmer. The basinet construction allows modern medical equipment to be positioned very near to the infant and yet provides a stable and nurturing environment for a new born baby to receive treatment. The linkage arrangement enables the space beneath the warmer to be more beneficially utilised and also reduces changes in distance between the infant and the radiant heat source, enabling temperature regulation of the infant to be more easily maintained.

We claim:

1. A partially enclosed article support structure comprising:

a support surface adapted to receive an article, at least one article retaining wall, at least one axle provided on said at least one article retaining wall, means for receiving said at least one axle provided on said support surface, wherein said at least one article retaining wall is rotatably attached to said support surface by the mounting of said at least one axle within said means for receiving said at least one axle thereby allowing said at least one article retaining wall to be rotated from a raised retaining position to a lowered article access position, and said at least one axle is slidable within said at least one article retaining wall to allow said at least one axle to be drawn within said at least one article retaining wall for detachment of at least one article retaining wall from said support surface.

2. A partially enclosed article support structure as claimed in claim 1 wherein said at least one axle is made from a rigid material and said means for receiving said at least one axle are formed from a compressible material, there being a tight frictional fit between said at least one axle and said means for receiving said at least one axle thereby allowing said rotation of said at least one article retaining wall to be damped due to said friction.

3. A partially enclosed article support structure as claimed in claim 1 wherein said means for receiving said at least one axle comprise a profiled hole and a compressible tubular damper inserted into said profiled hole, said compressible tubular damper substantially deforming to the shape of said profiled hole, and said at least one axle comprises a profiled stub wherein the cross-sectional shape of said profiled hole is large enough to accommodate said profiled stub in at least one position.

4. A partially enclosed article support structure as claimed in claim 3, wherein the cross sectional shape of said means for receiving said at least one axle is such that during rotation said profiled stub experiences a frictional opposing force which varies in magnitude according to the angular position of said profiled stub within said compressible tubular damper.

5. A partially enclosed article support structure as claimed in claim 3, wherein said profiled hole is substantially horse shoe shaped in cross-section.

6. A partially enclosed article support structure as claimed in claim 3, wherein said profiled stub is substantially race track shaped in cross-section.

7. A partially enclosed article support structure as claimed in claim 1, wherein said support surface comprises a rigid frame having an outer perimeter surrounding an open central portion, and flexible article support surface attached substantially around the entire said outer perimeter;

said rigid frame comprise a plurality of interconnected frame members, and means for connecting two adjacent said frame members, wherein an article may be positioned on and directly supported by said flexible article support surface and supported indirectly by said rigid frame and said means for connecting two adjacent said frame members include a projecting cover which covers said means for connecting two adjacent said frame members and extend outwardly therefrom and said means for receiving said at least one axle are provided on said projecting cover.

8. An infant warmer comprising:

a base, a support column having a lower end mounted on said base, a partially enclosed article support structure connected to said support column at a predetermined distance from said lower end, radiant heater connected to said support column, at a distance from said lower end greater than said predetermined distance, directed towards said partially enclosed article support structure, an inclination adjusting linkage arrangement connecting said partially enclosed article support structure to said support column, said linkage arrangement comprising:

a first linkage member having proximal and distal ends, pivotally connected to said support column at said proximal end at a first position on said support column, a second linkage member having proximal and distal ends, pivotally connected to said support column at said proximal end at a second position on said support column, there being a first predetermined distance between said first and second positions, wherein the distal ends of said first and said second linkage members are each pivotally connected to said partially enclosed article support structure at third and fourth positions respectively, there being a second predetermined distance between said third and fourth positions which is not equal to said first predetermined distance, the inclination of said partially enclosed article support structure relative to said support column thereby being selectable by pivotal movement of said first and second linkage members about said first, second, third and fourth positions, and said partially enclosed article support structure comprising:

a support surface adapted to receive an article, at least one article retaining wall, at least one axle proved on said at least one article retaining wall, means for receiving said at least one axle provided on said support surface, wherein said at least one article retaining wall is rotatably attached to said support surface by the mounting of said at least one axle within said means for receiving said at least one axle thereby allowing said at least one article retaining wall to be rotated from a raised retaining position to a lowered article access position.

9. An infant warmer as claimed in claim 8, wherein said support surface comprises a rigid frame having an outer perimeter surrounding an open central portion, a flexible article support surface having a continuous edge, beading attached to said flexible article support around a substantial part of said continuous edge, wherein said flexible article support surface is adapted to directly support an article which is supported indirectly by said rigid frame.

* * * * *